United States Patent
Stelmach

(10) Patent No.: US 7,475,694 B2
(45) Date of Patent: Jan. 13, 2009

(54) APPARATUS AND METHOD OF CLEANING TEETH

(76) Inventor: Thomas Stelmach, 11414 Thurston Cir., Los Angeles, CA (US) 90049

( * ) Notice: Subject to any disclaimer, the term of this patent is extended or adjusted under 35 U.S.C. 154(b) by 357 days.

(21) Appl. No.: 11/221,542

(22) Filed: Sep. 8, 2005

(65) Prior Publication Data

US 2007/0051386 A1 Mar. 8, 2007

(51) Int. Cl.
*A61C 15/00* (2006.01)
(52) U.S. Cl. .......................... 132/323; 433/4
(58) Field of Classification Search ............. 132/200, 132/321, 323; 433/3, 4; 606/144, 145, 147, 606/148

See application file for complete search history.

(56) References Cited

U.S. PATENT DOCUMENTS

| | | | | |
|---|---|---|---|---|
| 1,518,021 A | * | 12/1924 | Truxillo | ..................... 433/159 |
| 5,311,889 A | * | 5/1994 | Ringle et al. | ................. 132/321 |
| 5,560,377 A | * | 10/1996 | Donovan | ..................... 132/321 |
| 5,824,009 A | * | 10/1998 | Fukuda et al. | ............... 606/144 |
| 6,814,086 B2 | | 11/2004 | Stallings | |
| 2002/0169463 A1 | * | 11/2002 | Citron et al. | ................. 606/148 |

OTHER PUBLICATIONS

Oral-B website, Oral-B Super Floss, published at: http://www.oralb.com/us/products/product.asp?tid=products&sub=flossinterdental&cid=flossinterdental&pid=superfloss, 2006.

* cited by examiner

*Primary Examiner*—Todd E. Manahan
(74) *Attorney, Agent, or Firm*—Marc E. Hankin; Hankin Patent Law, APC

(57) ABSTRACT

This invention discloses an apparatus and method for cleaning teeth, particularly in individuals undergoing cosmetic and orthodontic treatment. The apparatus includes members having a tooth contact portion and a handle portion. Connected to the tooth contact portion is a floss tip enclosure element capable of receiving floss that is capped. The invention can be used easily and conveniently to enable a person to floss underneath bridges, or orthodontic wiring, without damage to the gingival tissue.

17 Claims, 4 Drawing Sheets

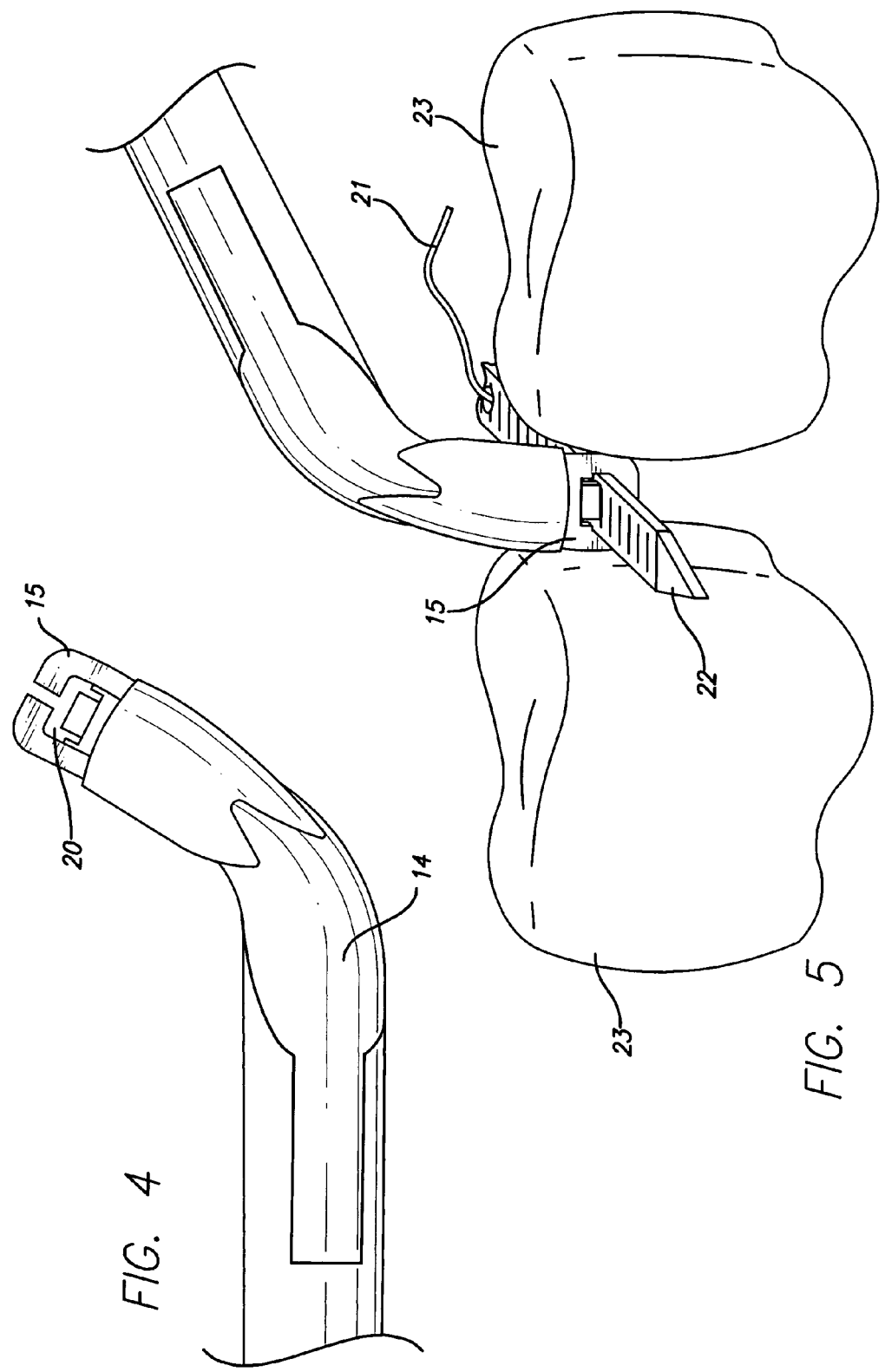

APPARATUS AND METHOD OF CLEANING TEETH

FIELD OF INVENTION

This invention relates, generally, to apparatuses for cleaning teeth; more particularly to apparatuses to clean teeth in individuals with implanted or attached cosmetic or orthodontic apparatuses.

BACKGROUND

A dental bridge is an appliance used to replace one or more missing teeth. These appliances typically are cemented into place and cannot easily be removed by the patient. The bridge normally is made to fill in an open space on the jaw inside the mouth, thus "bridging" the gap. There are several different types of dental bridges. In a traditional bridge, a pontic tooth (or false tooth) is held together by two crowns (a "cap" that covers the tooth, approximating its normal size and shape). This trio (or more if multiple missing teeth are being replaced) is then attached (cemented) to the abutment teeth (the surrounding teeth of each side of the gap). In a resin bonded bridge (also known as a "Maryland" bridge), the bridge involves the pontic (false) teeth being fused together to metal bands, bonded to the back of the abutment teeth with a resin cement. This type of procedure is common when the teeth missing are in the front of the mouth. Finally, a cantilever bridge is a type of procedure most appropriate when there are no abutment teeth on one side of the span.

To help eliminate, or reduce, any oral health problems while teeth are fixed with a bridge, dental care professionals recommend that teeth be brushed daily. Teeth should be brushed carefully after every meal with fluoride toothpaste and a soft-bristled toothbrush, as food may become lodged causing the gums and teeth to become infected. Infection may lead to further complications, possibly resulting in the loss of the bridge.

Brushing, however, is not sufficient to promote good dental hygiene. Dental floss is a thread-like product that is used to clean out the space between adjoining teeth as well as the spaces between a tooth and the adjoining soft tissue, known as the gingival or the gum.

Dental floss typically is made of round or flat, extra-strong, coated nylon fiber that is looped around the tooth, sliding in from the top, wedging into the space between the adjacent teeth. The floss is threaded in between the adjacent teeth and below the gingival sulcus. As the floss is pulled back and forth, it returns out of the gingival sulcus, removing plaque and bacteria from between the teeth and from below the gumline, thus sweeping out the debris, thereby creating a healthier oral environment.

The problem, however, is that flossing can be very difficult and tedious for individuals with implanted or attached cosmetic or orthodontic apparatuses, for example individuals with bridges or with orthodontic brackets affixed to the front portion of the teeth and a wire that connects each tooth together. This is because the bonding to the abutment tooth (in the case of bridges) or wire that connects from one tooth to another (in the case of orthodontic braces) generally prevents the floss from sliding in between the adjacent teeth from the top, as normally is the method. Thus, for such individuals, the floss needs to be placed underneath the bonding or wire and in front of the teeth to be able to floss the proximal surfaces of each tooth.

There are known in the prior art several means of inserting floss under bridgework and/or orthodontic brace wires. One such device is called a "floss-threader" which resembles a sewing needle. This device has a needle-like eye-loop for threading floss at the end of a piece of plastic that is more rigid than flexible, and can be placed under the bridge or wire. However, using such a device can be very difficult for many people, especially children and the elderly or infirm individuals.

Another product that can be used is the Oral-B™ brand "Super Floss®" (Oral B Laboratories, One Lagoon Drive, Redwood City, Calif., 94065) which is designed for individuals with fixed dental appliances, such as bridges, implants, or braces. "Super Floss®" has three sections: a stiffened end for easy threading under dental appliances, a spongy floss with which to clean around dental appliances, and a regular floss portion for cleaning around the natural teeth and under the gumline. The stiffened end may be used to thread a thin piece of floss under the bridge and it then can be pulled through until a thicker piece comes through, which can be used to clean under the bridge next to the gumline. The spongy floss may be threaded through a space between a tooth and a dental appliance, and then the spongy floss can be moved back and forth to clean the space. With a bridge, a sideways motion can be used to insert the floss and to clean between the bridge and the gum. Unfortunately, this requires good dexterity to accomplish.

Another means of inserting floss under bridgework and/or orthodontic brace wires is disclosed in U.S. Pat. No. 6,814,086. That device consists of a lead portion with a floss filament attached. The diameter of the flossing device is small enough to fit between the orthodontic wire and the front portion of the tooth. The soft coating and a curvilinear tip of the flossing guide protects the gingival tissue when inserted into a patient's mouth. However, increased dexterity is required to properly insert the device into the tiny clearance between teeth, and at the same time to concentrate on properly intruding the floss between the adjacent surfaces of two teeth. Unfortunately, such dexterity is beyond the capability of many juveniles who comprise the majority of orthodontic patients.

Therefore, there has been a long felt need for an apparatus that easily allows flossing of teeth, particularly for individuals having bridges or braces.

SUMMARY OF THE INVENTION

This invention is directed towards overcoming the above shortcomings by disclosing an apparatus that can be used easily and conveniently to enable an individual to floss underneath bridges, or orthodontic wiring, without excess effort and without causing damage to the gingival tissue.

An apparatus to clean teeth, in accord with the invention, comprises a first member including a first tooth contact portion connected to a first handle portion where the handle portion includes a location to apply pressure from, accommodate, or to receive a thumb; a second member pivotally connected to the first member and being disposed there beneath, where the second member includes a tooth contact portion and a handle portion, and where the handle portion includes a location to apply pressure from, accommodate, or to receive one or more fingers; and a floss tip enclosure element connected to the distal portion of the first tooth contact portion for holding one end of the floss wherein the head of the floss is covered by a cap; and a second floss tip enclosure element connected to the distal portion of the second tooth contact portion for receiving end of the floss from the first floss tip enclosure element; and a mechanism that is responsive to movement of members moving from the first to second positions that will drive the floss from one floss tip enclosure element through the gap between teeth, through to the other floss tip enclosure element.

In accord with one aspect, the apparatus to clean teeth is made of steel (such, as but limited to stainless steel and carbon steel). Alternatively, the apparatus can be made of an materials such as but not limited to alloys (such as, but not limited to, aluminum, and titanium), super alloys (such as but not limited to those made from chrome, cobalt, nickel and iron), ceramics, polymers (such as but not limited to thermoplastic and thermoset polymers), glass, wood, or metal plated with another metal.

In accord with another aspect of the invention, the thumb and finger-receiving members are curved. Advantageously, the thumb and finger-receiving members are elongated. In another aspect of the invention, the thumb and finger-receiving members are circular. Of course, any combination of the above is also possible. Alternatively, the handles could be straight.

In a preferred embodiment of the invention, there is a ratcheting component that responds to the movement of the members.

In accord with one aspect of the invention, the apparatus can be used to clean healthy teeth. Alternatively, the apparatus can be used to clean bridged teeth. Alternatively, the apparatus can be used to clean braced teeth.

In accord with another aspect of the invention, the apparatus can be used to clean teeth comprising the steps of inserting a cap with floss through first floss tip enclosure element of cleaning apparatus, positioning said apparatus alongside the gap between teeth to be cleaned, initiating a mechanism to thread cap from first floss tip enclosure element through the gap in between the teeth to the second floss tip enclosure element positioned along the tongue side of the mouth, releasing the floss tip from the apparatus, pulling the floss tip through from one side of the mouth to the other, moving the floss back and forth through the gap in the teeth with the fingers by holding floss at both ends, and removing the floss by pulling the floss completely through from one side of the mouth to the other side.

An advantage of the invention is that the user of the apparatus easily can thread floss into it and therefore a user does not have to thread floss through a tiny, hard-to-reach hole prior to use. Another advantage is that the apparatus can insert floss into areas of the mouth that are less accessible by hand. A further advantage is that the invention can be re-contoured into numerous shapes based on the mouth shape and/or hand size and the location of the bridgework. Another advantage is that the invention is easy and safe to use by people of all ages.

The foregoing, and other features and advantages of the invention, will be apparent from the following, more particular description of the preferred embodiments of the invention, the accompanying drawings, and the claims.

BRIEF DESCRIPTION OF THE DRAWINGS

FIG. 4 is a perspective side view of the tooth contact portion of the present invention.

FIG. 5 is a perspective side view of the invention as positioned between two teeth.

DETAILED DESCRIPTION OF THE DRAWINGS

In the following detailed description of various embodiments of the invention, numerous specific details are set forth in order to provide a thorough understanding of various aspects of one or more embodiments of the invention. However, one or more embodiments of the invention may be practiced without these specific details.

Figure 1:
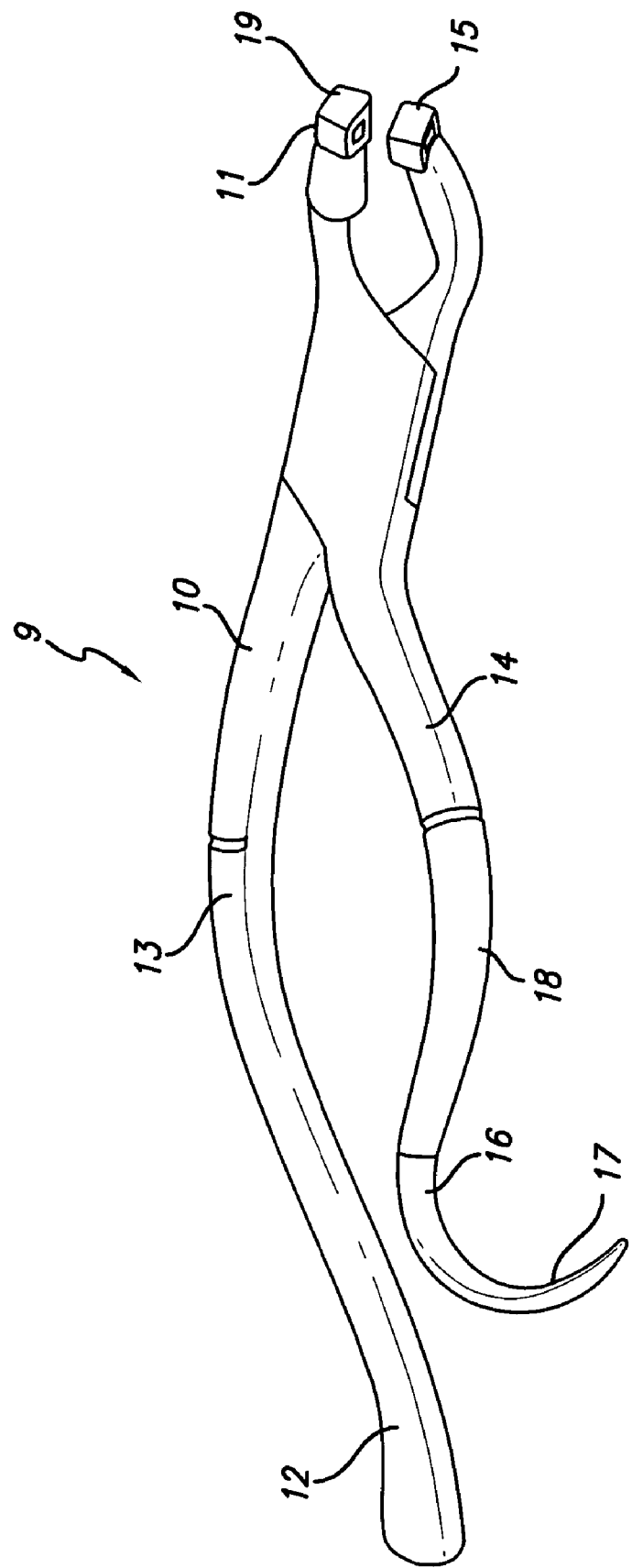
FIG. 1 is a perspective side view of one embodiment of the invention.
Figure 2:
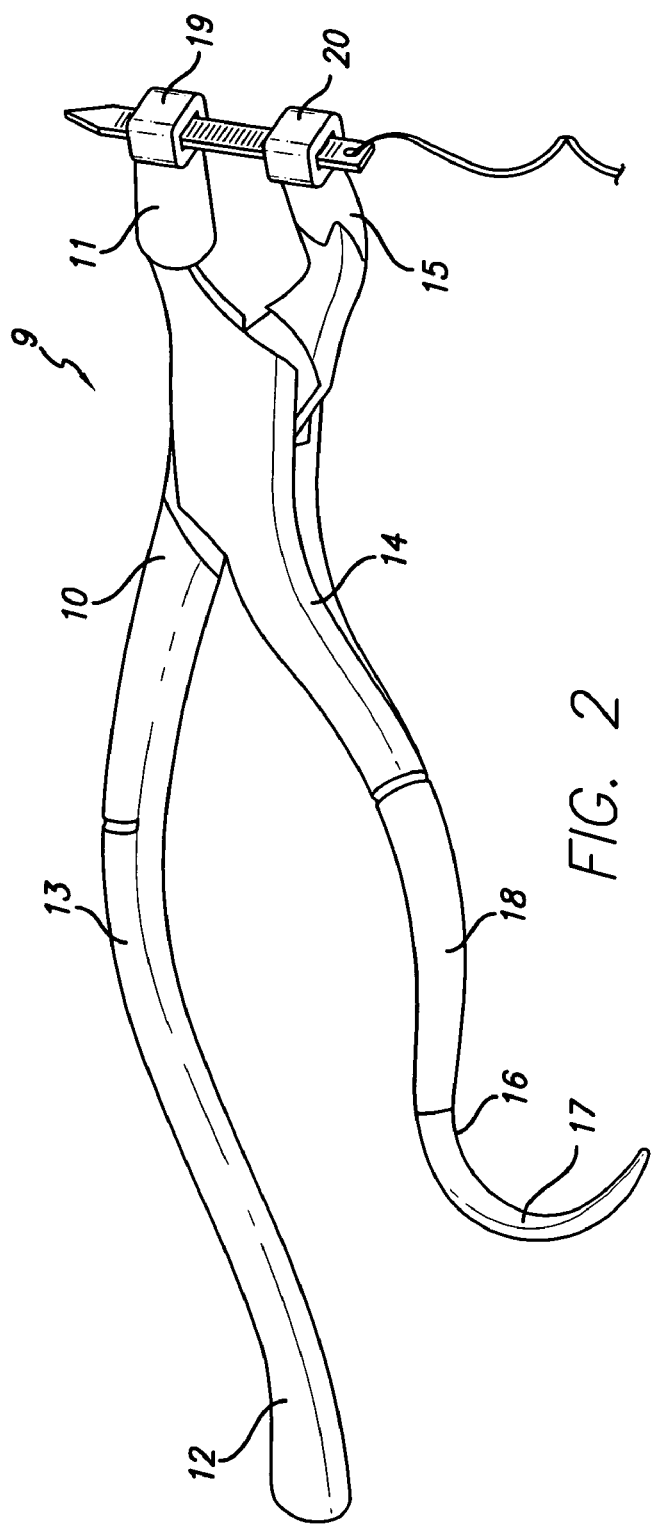
FIG. 2 is a front perspective view of one embodiment of the invention.

Referring initially to FIG. 1 and FIG. 2, the apparatus to clean teeth 9 includes a first member 10 with a tooth contact portion 11, a handle portion 12 and an engraved 13 section, integrated therewith. The apparatus to clean teeth 9 further includes a second member 14 pivotally connected to the first member 10 and disposed there beneath. The second member 14 includes a tooth contact portion 15 and a handle portion 16 and an engraved section, 18, integrated therewith. The engraved portions 13 and 18 are also areas within the members that can accommodate the user's thumb and fingers. In particular, a fastening member such as a conventional screw, for example, attaches the first and second members 10, 14 adjacent to their respective handle portions 12, 16. Of course, such members 10, 14 may vary in shape, and be made of various materials, as readily apparent to a person of ordinary skill in the art. Of course, both left-handed and right-handed users may employ the present invention, and it may be built a certain way to better accommodate left-handed users.

Notably, the handle portion 16 includes a thumb-receiving member 17. Advantageously, a user can operably move a thumb (not shown) into and out of the handle portion 17 quickly and easily.

Figure 3:
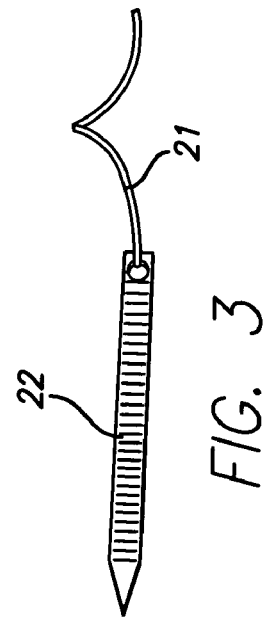
FIG. 3 is a perspective top view of the cap end of the floss.

FIG. 3 shows floss 21 is tied to a cap element 22. The cap element comprises of a ratchet-shaped teeth or saw-tooth portion and a hole that allows the floss to be treaded and tied.

The first floss tip enclosure element 20, within the tooth contact portion 15, comprises of an inner channel wall, an outer channel wall and a pair of sidewalls. The sidewalls define a cap 22 accepting channel which is able to engage the ratchet-shaped teeth portion of the cap when the cap 22 is inserted into the accepting channel in a certain orientation. Floss tip enclosure element 19 has an identical structure to floss tip element 20.

Teeth can be cleaned according to the following embodiment of the invention: The cap 22 is first positioned into the first floss tip enclosure element 20 in an orientation that allows the cap to be engaged. Then the first enclosure element is positioned on the cheek side of the tooth and the opposing second floss tip enclosure element 19, on the second member 10, is positioned on the tongue side of the tooth thereby sandwiching the tooth to be cleaned. Movement of the members by the user then initiates a ratcheting means which moves the cap, 22, with the floss, through the first floss tip enclosure element 20 and into the gum space. Continued movement of the members propels the cap 22 forward to engage the second floss tip enclosure element 19 on the tongue side of the tooth (see FIG. 5). Further movement of the members propels the cap completely through both the first tip enclosure element 20 and the second tip enclosure element 19. At this point, the cap unit can then be pulled through to disengage the second tip enclosure element 19 by the fingers of the user, whereby the user can then floss the tooth in a conventional back and forth motion. The structure of the cap unit and the enclosure tip elements as well as the ratcheting type mechanism is disclosed in U.S. Pat. No. 5,956,813 which is hereby incorporated by reference.

Although ratcheting type components and mechanisms are shown in this present embodiment of the invention, other structures and mechanisms that achieve a similar result are envisioned and may be apparent to one of ordinary skill in the art.

Figure 6:
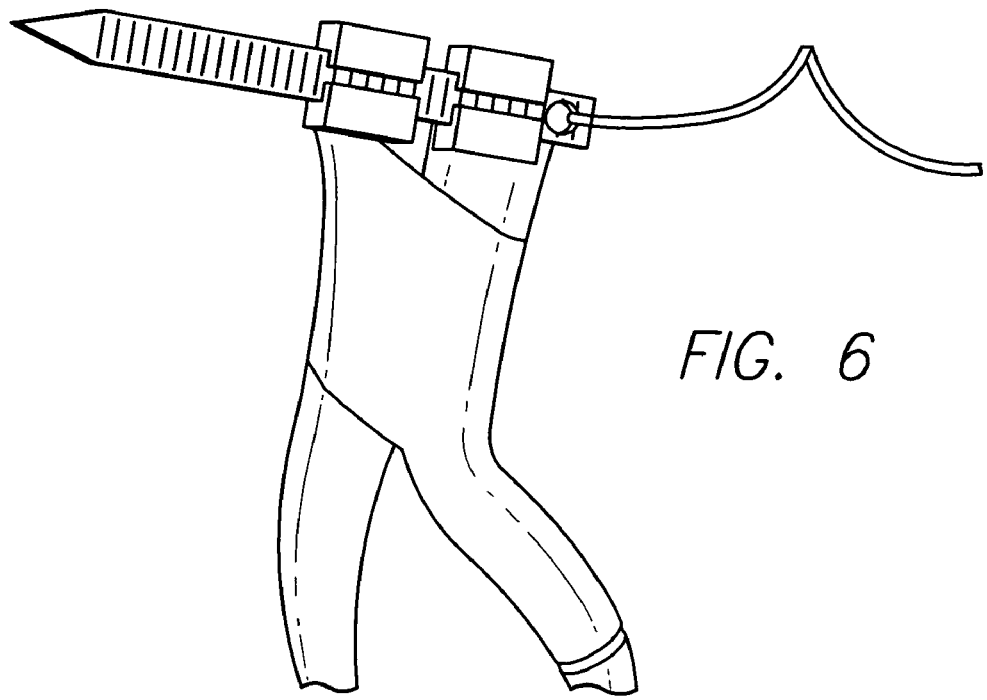
FIG. 6 is a perspective view of the members in the first position.
Figure 7:
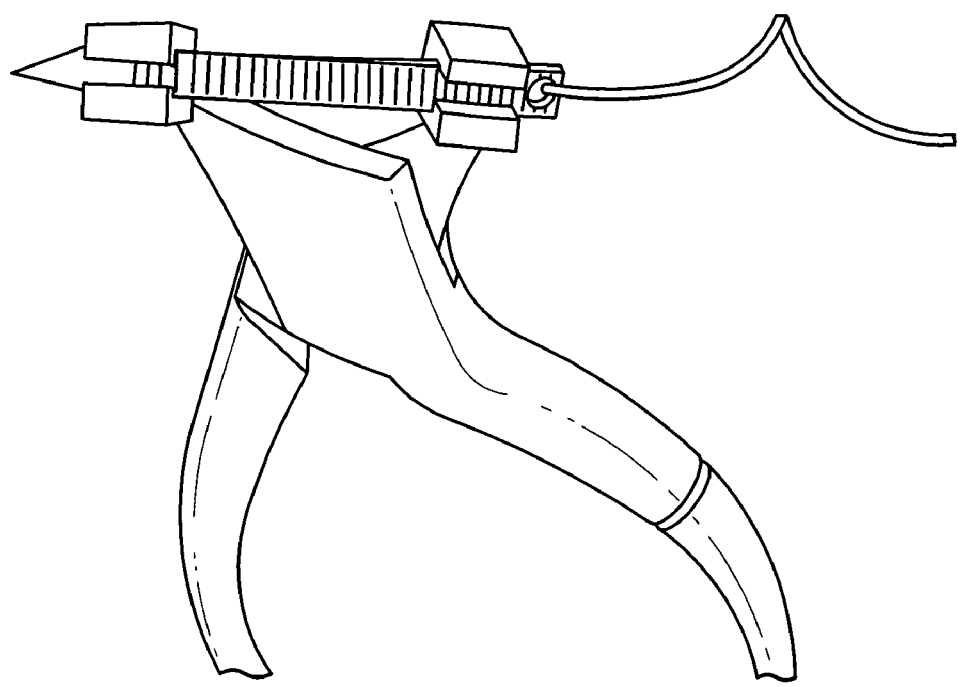
FIG. 7 is a perspective view of the members in the second position.

Members, 10 and 14 are connected by a pivoting means. The pivoting motion allows the first, 10, and second, 14, members to return to the first position (FIG. 6) after the members have been caused to move to the second position (see FIG. 7). In the ordinary course of using this invention, this pivoting motion will be repeated numerous times, essentially once for each space between every pair of adjacent teeth.

I claim:

1. An apparatus to clean teeth comprising:
    a first member including a first tooth contact portion and a first handle portion integrated therewith, said first handle portion including a location to apply pressure from, accommodate, or to receive a thumb; and
    a second member pivotally connected to said first member and being disposed there beneath, said second member including a second tooth contact portion and a second handle portion integrated therewith, said handle portion including a location to apply pressure from, accommodate, or to receive one or more fingers; and
    a pivoting means for connecting said first member to said second member, whereby the pivoting means allows said first and second members to return to a first position after said members have been caused to move to a second position;
    a first floss tip enclosure element connected to the distal portion of said first tooth contact portion for holding one end of a floss wherein the head of said floss is covered by a cap;
    a second floss tip enclosure element connected to the distal portion of said second tooth contact portion for receiving end of said floss from said first floss tip enclosure element;
    and means responsive to movement of members from said first to said second positions to drive said floss from said first floss tip enclosure element through the gap between teeth, through to said second floss tip enclosure element.
2. The apparatus to clean teeth of claim 1, wherein the first and second members are made of steel.
3. The apparatus to clean teeth of claim 1, wherein the first and second members are made of an alloy.
4. The apparatus to clean teeth of claim 1, wherein the first and second members are made of a polymer.
5. The apparatus to clean teeth of claim 1, wherein the first and second members are made of ceramic.
6. The apparatus to clean teeth of claim 1, wherein the first and second members are made of wood.
7. The apparatus to clean teeth of claim 1, wherein the locations to receive said thumb and said fingers are curved.
8. The apparatus to clean teeth of claim 1, wherein the locations to receive said thumb and said fingers are elongated.
9. The apparatus to clean teeth of claim 1, wherein the locations to receive said thumb and said fingers are straight.
10. The apparatus to clean teeth of claim 1, wherein the locations to receive a said thumb and said fingers are circular.
11. The apparatus to clean teeth of claim 1, wherein the first and second members each comprise of an engraved portion between the handle and tooth contact ends.
12. The apparatus to clean teeth of claim 1, wherein the gap between teeth is bounded by a dental bridge.
13. The apparatus to clean teeth of claim 1, wherein the gap between teeth is bounded by a dental brace.
14. The apparatus to clean teeth of claim 1, wherein said means responsive to movement of members is a ratcheting means.
15. A method of using an apparatus to clean teeth comprising the steps of:
    a. Inserting a floss cap with floss through a first floss tip enclosure element of the cleaning apparatus;
    b. Positioning said apparatus alongside a gap between teeth to be cleaned;
    c. Initiating the apparatus to thread the floss cap from the first floss tip enclosure element through the gap between teeth to a second floss tip enclosure element positioned along a tongue side of the mouth;
    d. Releasing the floss cap from the apparatus;
    e. Pulling the floss cap through from one side of the mouth to the other;
    f. Moving the floss back and forth through the gap in teeth with the fingers by holding floss at both ends.
    g. Removing the floss by pulling the floss completely through from one side of the mouth to the other side.
16. The method of using an apparatus to clean teeth of claim 15, wherein the gap between teeth is bounded by a dental bridge.
17. The method of using an apparatus to clean teeth of claim 15, wherein the gap between teeth is bounded by a dental brace.

* * * * *